United States Patent [19]

Arakawa et al.

[11] 4,442,037

[45] Apr. 10, 1984

[54] WATER-SOLUBLE CHOLESTEROL DERIVATIVE

[76] Inventors: Yoshio Arakawa, 10-18, Ezakacho 1-chome, Suita-shi; Atsuyuki Takanabe, 29-19, Nagao-Higashicho 2-chome; Yahiro Uemura, 5-18, Mitsuyacho, both of Hirakata-shi; Satoshi Funakoshi, 16-5, Aoyama 1-chome, Katano-shi; Tadakazu Suyama, 3-7, Tanabecho, Matsuigaoka 4-chome, Tsuzuki-gun, Kyoto, all of Japan

[21] Appl. No.: 432,938

[22] PCT Filed: Mar. 13, 1981

[86] PCT No.: PCT/JP81/00056

§ 371 Date: Sep. 28, 1982

§ 102(e) Date: Sep. 28, 1982

[87] PCT Pub. No.: WO82/03175

PCT Pub. Date: Sep. 30, 1982

[51] Int. Cl.$^3$ .............................................. C07J 9/00
[52] U.S. Cl. ...................................... 260/397.2; 424/177
[58] Field of Search ....................... 424/177; 260/397.2

[56] References Cited

U.S. PATENT DOCUMENTS 4,304,726  12/1981  Arakawa et al. ............... 260/397.2
4,379,779   4/1983  Rao et al. ........................ 260/397.5

Primary Examiner—Elbert L. Roberts

[57] ABSTRACT

Complexes of albumin combined with organic dibasic acid half esters, such as those of succinic acid and phthalic acid, of 7-hydroxycholesterol are soluble in water and have excellent immunosuppressive and anti-inflammatory action.

10 Claims, 2 Drawing Figures

WATER-SOLUBLE CHOLESTEROL DERIVATIVE

TECHNICAL FIELD

The present invention relates to water-soluble derivatives of cholesterol and more particularly to water-soluble derivatives of 7-hydroxycholesterol.

BACKGROUND ART

It is known that the immunoregulatory substance isolated from the Cohn IV, paste of human serum is 7-hydroxycholesterol and effective not only as an immunoregulatory agent, particularly acting to regulate cell-mediated immunity, but also as an anti-inflammatory agent (Japanese Patent Application Laid-open No. 104735/1978).

DISCLOSURE OF INVENTION

Since 7-hydroxycholesterol, a compound very valuable as a medicine, is sparingly soluble in water, the present inventors made intent studies aiming at development of its derivatives having improved water solubility.

As a result, the aim has been attained by finding out new compounds, complexes of albumin with organic dibasic acid half esters of 7-hydroxycholesterol.

Thus, the object of this invention is to provide said complexes, which are represented by the formula

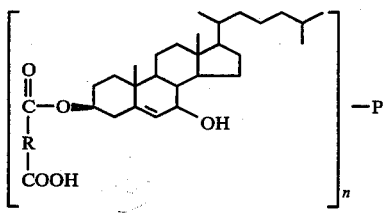

wherein R is phenylene or $(CH_2)_m$, of which m indicates 0 or an integer of 1-5, P is albumin residue, and n is a number of 20-200, which indicates the number of moles of the steroid, shown in the bracket, binding to mole of albumin.

Figure 1:
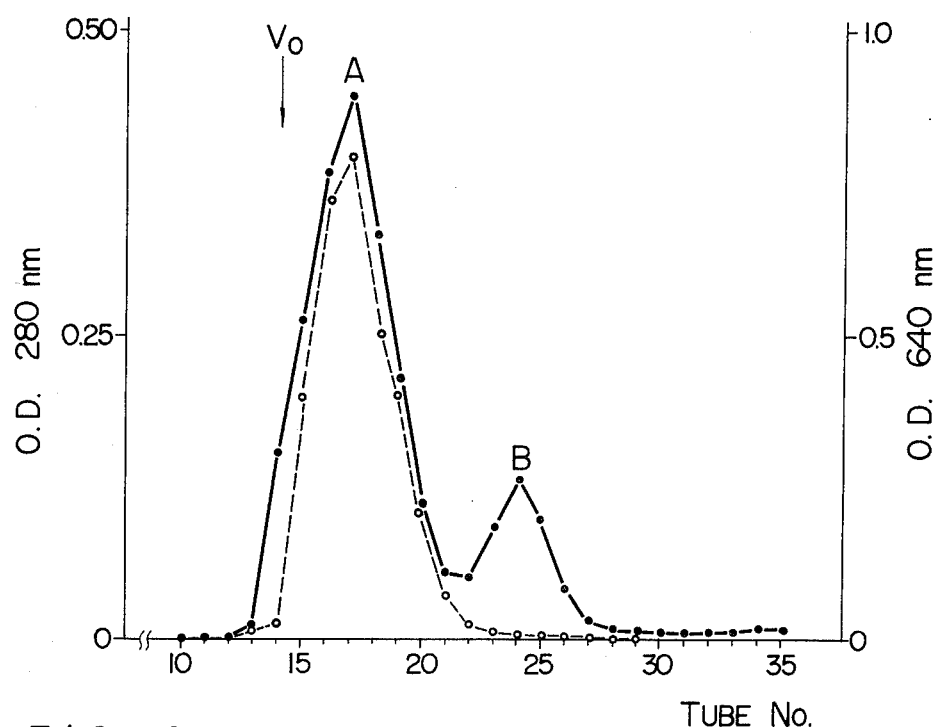
FIGS. 1 and 2 show results of gel filtration of the respective compounds obtained by reacting 1 part of albumin and 3 parts of albumin, respectively, to 1 part of 7-hydroxycholesterol-3-succinic acid half ester.

In these figures, concentrations of albumin are represented by measured values of the O.D. (optical density) at 280 nm (     ), concentrations of 7-hydroxycholesterol-3-succinic acid half ester are represented by measured values of the O.D. at 640 nm (· · ·) after development of color by the Lubschutz reaction, and peak A, peak B, and $V_o$ correspond to the complex, the unreacted albumin, and the void volume, respectively.

BEST MODE FOR CARRYING OUT THE INVENTION

An organic dibasic acid half ester of 7-hydroxycholesterol, used as a starting material in this invention, which is represented by the formula

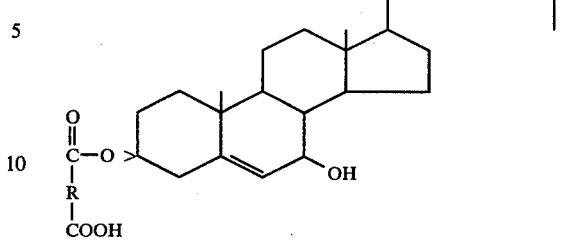

wherein R is as defined above, can be prepared from 7-ketocholesterol by esterifying it with a reactive derivative of the corresponding organic dibasic acid in the presence of a tertiary amine, followed by the reduction with a complex metal hydride (Japanese Patent Application No. 7676/1979). Preferred organic dibasic acids used include succinic acid and phthalic acid, and preferred starting materials include 7-hydroxycholesterol-3-succinic acid half ester, 7-hydroxycholesterol-3-phthalic acid half ester, and 7β-hydroxycholesterol-3-phthalic acid half ester.

The compounds of this invention are conveniently produced by uniform reaction of half esters above mentioned with albumin in a mixture of water and a water-misible organic solvent such as dioxane, tetrahydrofuran, or dimethylsulfoxide. Water is a good solvent for albumin and the organic solvent is so for the half ester. Thus, the reaction is carried out in such a way that such an organic solvent is added to an aqueous solution of albumin and then a solution of the half ester in the organic solvent is added to the resulting mixture with stirring or in the reverse addition order. Organic solvent to water ratios allowing enough uniform progress of the reaction are acceptable, which are 1:1-10.

The albumin to be used may be of human or bovine serum, and it is not particularly restricted as far as purified for therapeutic purposes. Needless to say, those of human derivation are preferred. The purity of the albumin is preferably not less than 80% as measured by the electrophoretic method. The amount of albumin used for preparation is chosen from within the range of 0.2-10 parts by weight for part by weight of the organic dibasic acid half ester of 7-hydroxycholesterol, so that the complex having a desired binding ratio can be obtained. An increase in the proportion of albumin makes the water-solubility of the half ester increased, but this is unfavorable with respect to therapeutic efficacy since it decreases the half ester content at the same time. It is more favorable to bind a maximum possible amount of the half ester to one mole of the albumin. The binding molar ratio is 20-200 moles, preferably 50 moles of more, of half ester to mole of albumin. In order to increase the binding ratio, the amount of half ester added may be increased, thereby a desired result being obtained.

The reaction temperature, though not particularly limited, is usually 0°-10° C. In consideration of the solubility of albumin, the reaction is desirable to be carried out in an alkaline region. Accordingly, for instance, a small amount of NaOH is added to the reaction system to adjust the pH to 8-10. A reaction time of 1-5 hours is adequate. A longer reaction time has no particular effect.

The reaction liquid obtained is freed from unreacted reactants as required. For removing them, known techniques can be applied. A preferred technique for this purpose is gel filtration, wherein the carrier to be used is not particularly restricted as far as suited to the separation of protein. A wide variety of gel filtration carriers fitted to the molecular weight of serum albumin (about 64,900) can be utilized. As examples thereof, there may be cited Sephadex (crosslinked dextran) G-200, G-150, and G-100 and Sepharose (agarose) 4B and 6B (supplied by Pharmacia, Ltd., Sweden).

The unreacted albumin and half ester may be incorporated with the complex in preparations without separation. In particular, free albumin has a stabilizing effect on preparations when contained therein in suitable amounts (0.01–10 wt%).

The water-soluble derivative of cholesterol thus obtained is then made up to preparations according to a desired known preparation method. For instance, the resulting liquid is then dialyzed against a buffer solution to be desalted, and the desalted inner liquid is recovered, subjected to sterilizing filtration, if necessary, and lyophilized to dry preparations. The buffer solution used in the dialysis is preferably adjusted to pH 7.0–8.0. For example, phosphate buffer, citrate buffer, and acetate buffer can be used for this purpose. The ionic concentration is 0.001–0.1 M.

The preparations of this invention may contain, as desired, known adjuvants such as carrier, excipient, dissolving aid, and stabilizer, which are added according to conventional methods. A preferred form of the preparations in application thereof as a therapeutic agent is an injectable one, and the dose in this case is 10–1000 mg/Kg as organic dibasic acid half ester of 7-hydroxycholesterol. When applied as an injection medicine, the present preparations are preferably dissolved each time in water to use as an 0.1–20% aqueous solution. The present preparations are, of course, available as medicines for external application and for oral application.

The complexes thus obtained of albumin with organic dibasic acid half esters of 7-hydroxycholesterol are new compounds unreported in the literature, and exhibit excellent efficacy in immunoregulation, especially in suppression of cel-mediated immunity and in anti-inflammation. Moreover, they readily dissolve in water forming a clear, stable, and neutral solution, and are therefore very useful as pharmaceuticals.

Experiment data on the usefulness of the compound of this invention will be shown below which were prepared in the following Example 1 but not yet subjected to gel filtration.

(1) Immunoregulatory action (tests in vitro)

The 50% inhibitory concentration of the compound of this invention in the PHA reaction according to S. R. Cooparband et al. [The Journal of Immunology, 109, No. 1,154 (1972)] was tested. The result is shown in Table 1. Additionally, the result of the same test on the immunoregulatory α-globulin (IRA) obtained by the method of Occhino et al. [The Journal of Immunology, 110, (3) (1973)] is shown for comparison.

TABLE 1

| Sample | 50% inhibitory concentration in the PHR reaction (μg/ml) |
| --- | --- |
| Complex of albumin with | 3 |
| 7-hydroxycholesterol-3-succinic acid half ester | (as steroid) |
| IRA | 20 |

(2) Immunoregulatory action (tests in vivo)

Animal tests were carried out using five mice for each sample. An aqueous solution of the complex of albumin with 7-hydroxycholesterol-3-succinic acid half ester (8 mg/Kg/day as steroid), an aqueous solution of albumin (8 mg/Kg/day), and saline as a control were intravenously injected into mice during 20 days in succession to examine the effect of each sample on the transplantation of skin. The mode of administration was as follows: to each rat a dose was given 24 hours before the skin transplantation and thereafter the administration of a dose per day was continued for 20 days. According to the 20-days later observation of surface, the percentage of successful grafts was 0% for the control, about 5% for the albumin, and about 80–90% for the complex of this invention. This indicates pharmacological therapeutic effectiveness of the complex as an immunoregulatory agent.

(3) Anti-inflammatory action

Animal tests were carried out using five rats for each sample. An aqueous solution of the complex of albumin with 7-hydroxycholesterol-3-succinic acid half ester was injected into the abdominal cavity of each rat (50 mg/Kg as steroid) and 1 hour later 0.05 ml of 1% aqueous carrageenin was hypodermically inoculated as an inflammatory agent to a hind leg of each rat. Four hours after inoculation of carrageenin, the volume of the edema formed on the leg was measured by means of a volume differential meter, and on the volume of edema the complex was compared with the reference sample albumin (a dose: 50 mg/Kg) and with the control saline. The results are shown in Table 2.

TABLE 2

| Sample | Increase in volume of edema (%) |
| --- | --- |
| Saline | 82 |
| Albumin | 78 |
| Complex of albumin with 7-hydroxycholesterol-3-succinic acid half ester | 28 |

(4) Acute toxicity test

Acute toxicity was tested on the present compound using each group of five rats each weighing about 200 g. The compound in the form of aqueous solution was abdominally injected in doses of 250, 750, and 1000 mg/Kg as weight of steroid for respective groups of rat. As a result of five days observation, no case of death was found.

Thus, the compound of this invention is almost non-toxic and not antigenic so that it can be provided as an excellent immunoregulatory agent or anti-inflammatory agent.

The present invention will be illustrated by the following reference example of preparation of starting material and examples of carrying out the invention.

Reference Example 1 (preparation of starting material)

(1) After 5 g of 7-ketocholesterol was dissolved in 50 ml pyridine, 1.8 g of succinic anhydride was added thereto, the mixture was heated to react for 8 hours at 90° C. and allowed to stand at room temperature overnight. Then, the resulting liquid was poured into 500 ml ice-cold water. The crystals precipitated by acidification with hydrochloric acid were collected by filtration and then dissolved in ethanol, active carbon was added thereto for decoloration and filtered off, water was added to the filtrate, and the precipitated crystals were recovered by filtration. Upon recrystallization thereof from aqueous ethanol, 5.4 g of 7-ketocholesterol succinic acid half ester was obtained as flaky crystals, m.p. 187.5°–189.5° C.

Elemental analysis:
Calcd. for $C_{31}H_{48}O_5$: C, 74.36; H, 9.66, Found: C, 74.54; H, 9.59.

I.R. absorption spectrum (KBr tablet): 1735, 1705, 1670, 1170 cm$^{-1}$.

(2) While stirring, 820 mg sodium borohydride was slowly added to a solution of 3.75 g sodium salt of 7-ketocholesterol succinic acid half ester in 100 ml methanol under cooling with ice. Stirring was continued for 10–15 minutes with ice-cooling and for further 1 hour at room temperature. The resulting liquid, after excess sodium borohydride was decomposed by adding 2 ml acetic acid, was diluted with 150 ml water and acidified with hydrochloric acid. Precipitated crystals were filtered and recrystallized from cyclohexane. Thus, 3.43 g of 7-hydroxycholesterol-3-succinic acid half ester was obtained as needle-like crystals, m.p. 150°–154° C. This product was a mixture of 7α-hydroxy and 7β-hydroxy forms in a ratio of about 1:3, the latter being major.

Elemental analysis:
Calcd. for $C_{31}H_{50}O_5$: C, 74.06; H, 10.02, Found: C, 74.21; H, 9.96.

I.R. absorption spectrum (KBr tablet): 3500, 1730, 1705, 1165 cm$^{-1}$.

EXAMPLE 1

A solution of 900 mg human serum albumin in a mixture of 60 ml water, 0.9 ml 1 N NaOH, and 30 ml dioxane was slowly added to a solution of 900 mg 7-hydroxycholesterol-3-succinic acid half ester in 21 ml dioxane while stirring at 5°–10° C., and stirring was continued for 3 hours. Thereafter the resulting liquid was dialyzed against 0.05 M phosphate buffer (pH 7.4) at 5°–10° C. for 24 hours. Upon lyophilization of the dialized inner solution in vacuo, 2.9 g of a white dry powder was obtained.

Physicochemical properties of this product are as follows:

Herein the 7-hydroxycholesterol-3-succinic acid half ester constituent was determined by gas chromatography through the alkali hydrolysis into 7-hydroxycholesterol followed by tetramethylsilyl substitution in the known way, and the albumin constituent was determined by the Lowry method.

(1) Composition:
7-hydroxycholesterol-3-succinic acid half ester: 29.14%
Albumin: 33.10%.
Phosphate: 37.76%.

(2) Binding steroid: 117.5 mol/mol of albumin,
(3) Solubility: 200 mg/ml of $H_2O$,
(4) pH: 7.4 (2% aqueous solution).

Results of the gel filtration through Sephadex G-200 are shown in FIG. 1.

While this product showed its enhanced usefulness in the foregoing animal tests, 2 g of a further purified product was obtained therefrom by gel filtration. Conditions of the gel filtration were as follows:

Gel filtration carrier: Sephadex G-200
Column: K 16/70,
Bed capacity: 120 ml (1.6×60 cm),
Eluent: 1/15 M phosphate buffer, pH 7.4, (containing 0.01% of $NaN_3$),
Flow rate: 6.0–6.5 ml/hr,
Fraction: 3.0 ml/tube.

EXAMPLE 2

A solution of 2.7 g human serum albumin in a mixture of 180 ml water, 2.7 ml 1 N NaOH, and 90 ml dioxane was slowly added to a solution of 900 mg 7-hydroxycholesterol-3-succinic acid half ester in 21 ml dioxane while stirring at 5°–10° C., and stirring was continued for 3 hours. Thereafter, in the same manner as in Example 1, 6.8 g of a dry powder was obtained.

Physicochemical properties of this product are as follows:

(1) Composition:
7-hydroxycholesterol-3-succinic acid half ester: 12.03%,
Albumin: 41.31%,
Phosphate: 46.66%,
(2) Binding steroid: 38.9 mol/mol of albumin,
(3) Solubility: 250 mg/ml of $H_2O$,
(4) pH: 7.4 (2% aqueous solution).

Figure 2:
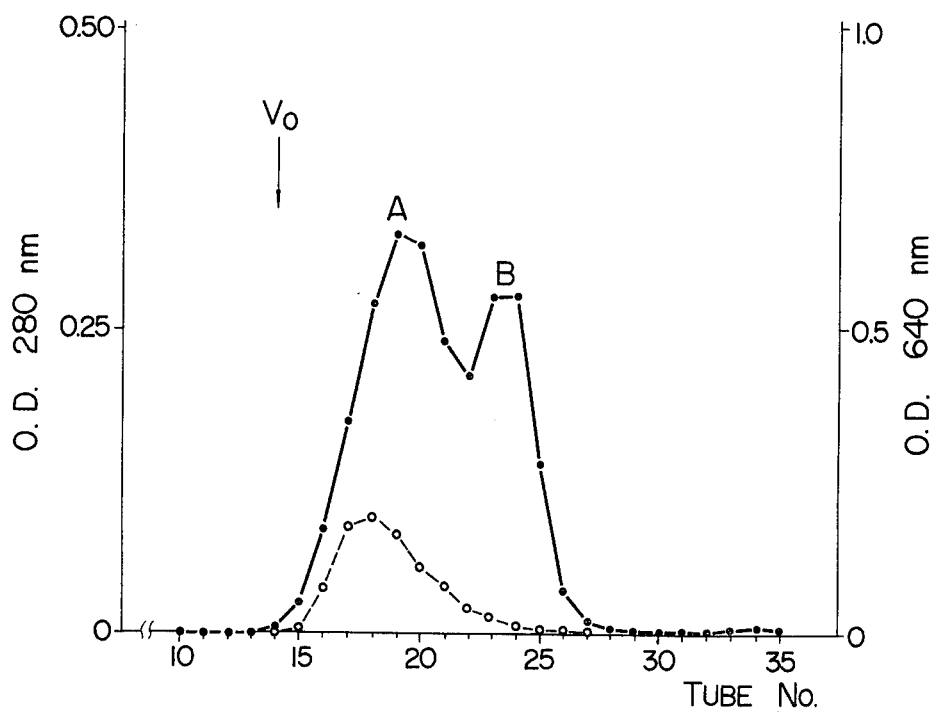

By the same gel filtration procedure as in Example 1, 6 g of a purified product was obtained. Results of the gel filtration are shown in FIG. 2.

We claim:

1. A complex of albumin with an organic dibasic acid half ester of 7-hydroxycholesterol, said complex being represented by the formula

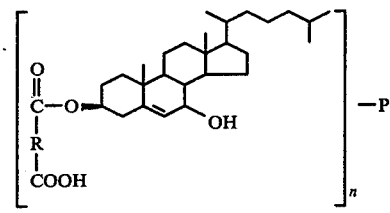

wherein R is phenylene or $(CH_2)_m$, of which m indicates 0 or an integer of 1–5, P is albumin residue, and n is a number of 20–200 indicating the number of moles of the steroid, shown in the bracket, binding to mole of albumin.

2. A process for preparing a complex of albumin with an organic acid half ester of 7-hydroxycholesterol, said complex being represented by the formula

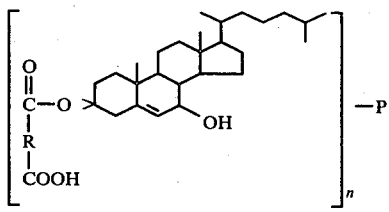

wherein R is phenylene or $(CH_2)_m$, of which m indicates 0 or an integer of 1-5, P is albumin residue, and n is a number of 20-200 indicating the number of moles of the steroid, shown in the bracket, binding to mole of albumin, said process comprising reacting albumin with a dibasic acid half ester of 7-hydroxycholesterol represented by the formula

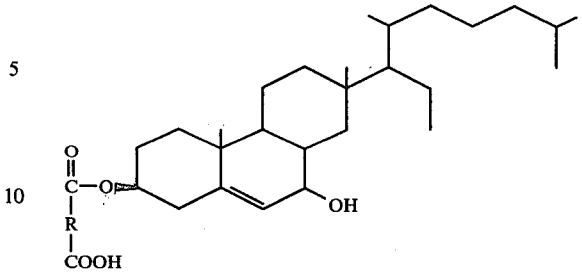

wherein R is as defined above, and recovering the reaction product.

3. A process according to claim 2, wherein 0.2-10 parts by weight of albumin is used per part by weight of the organic dibasic acid half ester of 7-hydroxycholesterol.

4. A process according to claim 2, wherein the reaction is carried out in a mixed medium of water and a water-miscible organic solvent.

5. A process according to claim 2, wherein the reaction is carried out using 20-200 moles of the organic dibasic acid half ester of 7-hydroxycholesterol per mole of albumin.

6. A process according to claim 2, wherein the recovery of reaction product is carried out by gel filtration to separate from the free albumin.

7. A composition for transplantation of organ, containing a water-soluble complex of claim 1 of albumin with an organic dibasic acid half ester of 7-hydroxycholesterol.

8. A composition for treating inflammation, containing a water-soluble complex of claim 1 of albumin with an organic dibasic acid half ester of 7-hydroxycholesterol.

9. Use for transplantation of organ of a water-soluble complex of claim 1 of albumin with an organic dibasic acid half ester of 7-hydroxycholesterol.

10. Use for treating inflammation of a water-soluble complex of claim 1 of albumin with an organic dibasic acid half ester of 7-hydroxycholesterol.

* * * * *

UNITED STATES PATENT AND TRADEMARK OFFICE
CERTIFICATE OF CORRECTION

PATENT NO. : 4,442,037
DATED : April 10, 1984
INVENTOR(S) : ARAKAWA et al

It is certified that error appears in the above—identified patent and that said Letters Patent is hereby corrected as shown below:

On the title page insert:

-- [73] Assignee: The Green Cross Corporation, Osaka, Japan --

Signed and Sealed this

Twentieth Day of November 1984

[SEAL]

Attest:

Attesting Officer

GERALD J. MOSSINGHOFF

Commissioner of Patents and Trademarks